United States Patent [19]
Kaminski et al.

[11] Patent Number: 5,640,957
[45] Date of Patent: Jun. 24, 1997

[54] ULTRAVIOLET RADIATION PROTECTION EVALUATOR

[75] Inventors: Ray Kaminski, Brick, N.J.; Nikiforos Kollias, Belmont, Mass.

[73] Assignee: Instruments SA, Inc., Edison, N.J.

[21] Appl. No.: 488,502

[22] Filed: Jun. 9, 1995

Related U.S. Application Data

[63] Continuation of Ser. No. 128,999, Sep. 29, 1993, abandoned.

[51] Int. Cl.⁶ ............................................. A61B 5/05
[52] U.S. Cl. .................. 128/653.1; 128/665; 128/633
[58] Field of Search .............................. 128/630, 633, 128/653.1, 664, 665; 607/94; 250/372

[56] References Cited

U.S. PATENT DOCUMENTS

| | | | |
|---|---|---|---|
| 4,423,736 | 1/1984 | DeWitt et al. | 128/633 |
| 4,882,598 | 11/1989 | Wulf | 250/372 |
| 4,894,547 | 1/1990 | Leffell et al. | 128/633 |
| 5,201,318 | 4/1993 | Rava et al. | 128/665 |

FOREIGN PATENT DOCUMENTS

| | | | |
|---|---|---|---|
| 2218802 | 11/1989 | United Kingdom | 250/372 |
| 2236182 | 3/1991 | United Kingdom | 250/372 |

OTHER PUBLICATIONS

"Biological Responses to Ultraviolet A Radiation"; from the symposium of the Second International Conference of the American Society for Photobiology, Jun. 27–28, 1991; Copyright 1992 (Valdernmar Publishing Company).

*Primary Examiner*—Marvin M. Lateef
*Assistant Examiner*—Brian L. Casler
*Attorney, Agent, or Firm*—Handal & Morofsky

[57] ABSTRACT

An ultraviolet radiation protection evaluator for determining the effectiveness and protection rating of sunscreen. The apparatus contains a fiber optic probe for delivering Ultraviolet radiation directly to skin. The probe receives reflected and diffused ultraviolet radiation from the skin and transmits the same to a monochromator which performs a spectral analysis and evaluation on the reflected radiation. This information is transmitted to a computer having software for evaluating the readings. The readings are taken first on untreated skin then again on skin treated with a sunscreen. The software, via variables inputted to the computer, computes the ratio of the sunscreen data obtained from both the treated and untreated skin along with the product of the spectrum of the light and radiation source and the action spectrum of UV induced erythema and qualitively characterizes the sunscreen in relation to natural skin protection.

21 Claims, 7 Drawing Sheets

ULTRAVIOLET RADIATION PROTECTION EVALUATOR

This application is a continuation of application Ser. No. 08/128,999, filed Sep. 29, 1993, now abandoned.

TECHNICAL FIELD

This invention relates to lotion and other types of sunscreens, and more particularly, to an apparatus for evaluating the effectiveness and determining the appropriate sun protection factor (SPF) rating of such sunscreens.

BACKGROUND OF THE INVENTION

Recent discoveries in the medical field regarding skin cancer and the role of the sun in causing the same have made sunscreens more popular than ever. Moreover, the alarming rate at which the ozone layer was depleted and the slow rate of recovery makes advances in sunscreen technology an important and potentially lifesaving science. Commercially available sunscreens range in potency from two times the skin's naturally occurring UV protection to thirty five and more times the natural state.

Measuring the effectiveness of sunscreens is imperative to rating existing sunscreens with relation to their improvement of the skin's natural abilities and for determining the value of new compositions with regard to the same. The most popular techniques for evaluating sunscreens include in vivo phoyo testing or in vitro transmission methods.

Phototesting involves exposing a portion of a living person's skin to ultraviolet radiation and measuring for a given amount of ultraviolet radiation the time necessary to produce sunburn of a given degree of severity to treated and untreated portions of the subject's skin. More particularly, the amount of time necessary to produce the sunburn without a protective application of sunscreen is noted. The amount of time necessarily increases with the application of sunscreen and the measure of this amount divided by the amount without sunscreen provides the sun protection put on or SPF of the sunscreen.

However, such an approach suffers from a number of problems and limitations. In particular, this method is time consuming. It is also substantially non-reproducible. Naturally, the process is also painful to the subject. As a result of the pain involved, an additional problem includes finding living persons who will willingly submit to such testing. Finally, the evaluation of the degree of the sunburn is a subjective visual evaluation of the irritation.

The other method of evaluation is by in vitro transmission. Solid supports or substrates are coated with the sunscreen, exposed to ultraviolet radiation and a transmission spectrum is taken and compared to similar measurements for non-coated solids or substrates. The problem with this method is that possible reactions by the skin to the sunscreen are not detected.

Equally important to protection, is the evaluation of the ability of the skin to take advantage of the sunscreen's characteristic of improving its ability to protect itself from harmful ultraviolet radiation. That is, while particular sunscreens may provide five times the natural protection to one group of people, it may only provide three times the body's natural protection to another group. In vitro testing is ineffective for this determination.

The current invention solves the problems associated with the above methods of sunscreen evaluation by using live subjects and a machine to measure the effects of ultraviolet radiation with and without sunscreen, and without having to resort to burning.

SUMMARY OF THE INVENTION

The ultraviolet radiation protection evaluator as claimed is intended to provide a remedy. It solves the problem of the current lack of tests for determining the effectiveness of sunscreens in comparison to a body's natural protective abilities and for determining sun damage susceptibility to individuals without inaccuracies and without inflicting pain.

The ultraviolet radiation protection evaluator disclosed herein allows for the testing of the effectiveness of sunscreens in improving the body's natural ability to protect against harmful radiation. The evaluator is substantially harmless and individually accurate.

In accordance with the invention, the apparatus comprises an optical probe for delivering ultraviolet radiation directly to skin. The probe receives returned and diffused ultraviolet radiation from the skin and transmits the same to a monochromator which performs a spectral analysis and evaluation of the returned radiation.

The readings are taken first on untreated skin then again on skin treated with a sunscreen. This information is transmitted to a computer having software for evaluating the readings. The software computes the ratio of the sunscreen data obtained from both the treated and untreated skin and quantitatively characterizes the sunscreen's ability to multiply the effects of the natural skin to protect itself.

BRIEF DESCRIPTION OF THE DRAWINGS

One way of carrying out the invention is described in detail below with reference to drawings which illustrate only one specific embodiment, in which.

BEST MODE FOR CARRYING OUT THE INVENTION

Figure 1:
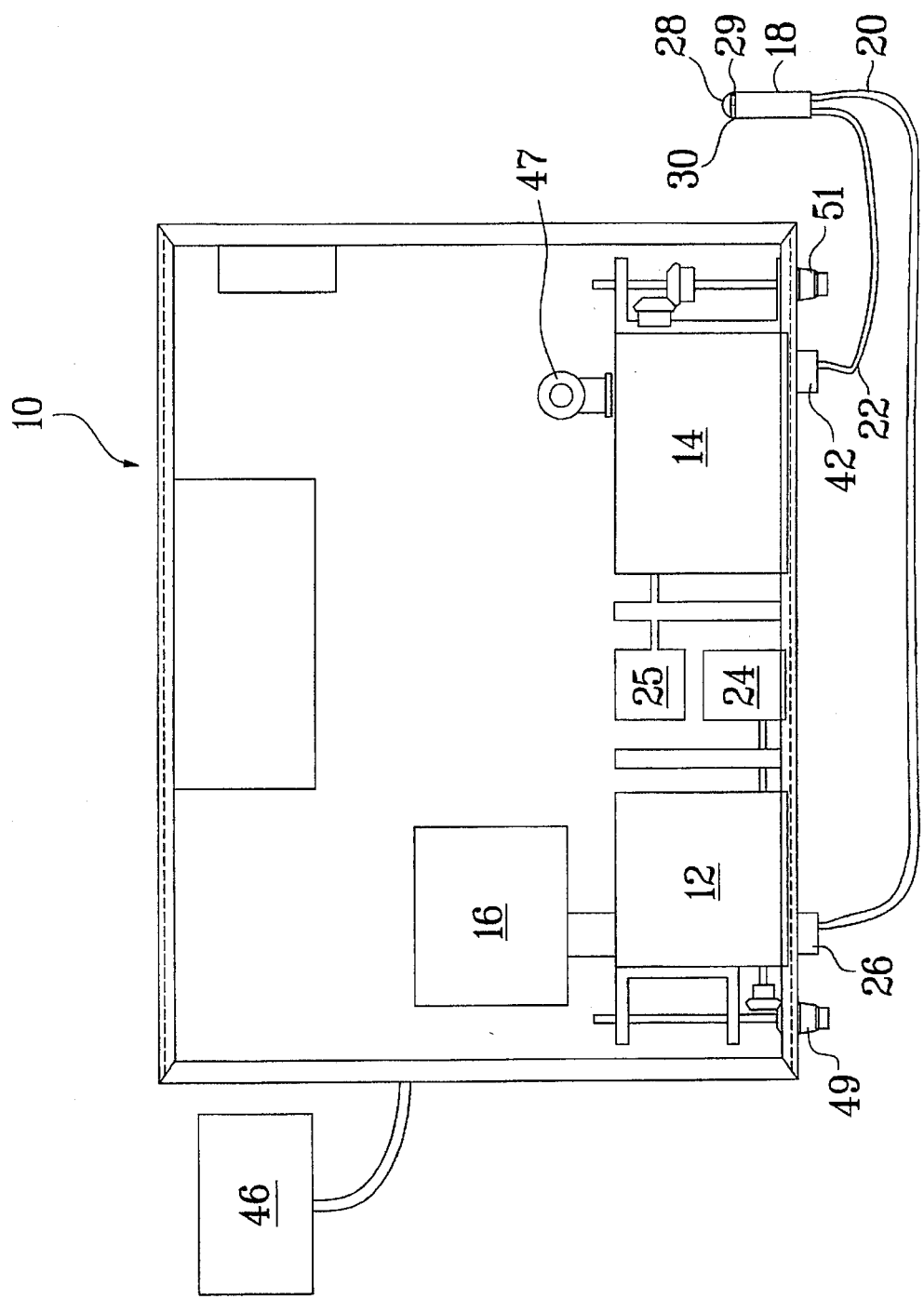
FIG. 1 is a top plan view of an ultraviolet radiation protection evaluator in accordance with the present invention.

Referring to the drawings in detail, wherein like reference numerals have been used throughout the various figures to designate like elements, there is shown in FIG. 1 a top plan view of the ultraviolet radiation protection machine designated generally as 10. The evaluator 10 is comprised generally of the source monochromator 12, a detector monochromator 14 and lamp 16. Lamp 16 is optically coupled to source monochromator 12. A fiber optic probe 18 is optically connected to both the source and detector monochromator by way of fiber optic bundles 20 and 22.

Source monochromator 12 is coupled to lamp 16 for receiving light radiation therefrom. The source monochromator 12, shown in FIGS. 1, 4 and 8, receives light and radiation from lamp 16 and separates therefrom a narrow band of radiation selected from the violet and ultraviolet wavelengths. Preferably, one uses an in line optical path monochromator having a 32×33 mm grating, which is an abberation corrected, concave holographic grating with a 100 mm focal length with a groove density of 1200 grooves per millimeter. Prefabricated modules, such as the monochromator sold by Instruments SA, Inc. of Edison, N.J. under the trademark H-10 may be used for monochromators 12 and 14.

Monochromators 12 and 14 each have respective stepper motors 24 and 25 mechanically coupled thereto so as to allow automatic wavelength scanning. Motors 24 and 25 are computer controlled to put monochromators 12 and 14 at the same wavelength. The specifications of monochromators 12 and 14 should be such that the ultraviolet band can be scanned for transmission to fiber optic bundle 22. In use, monochromators 12 and 14 scan the band between 280 and 400 nanometers. If effectiveness in the UVA region of 320–400 nanometers is to be measured, this range is scanned. Alternatively, the UVB range may be scanned and effectiveness in this range measured. Accordingly, source monochromator 12 separates out the harmful ultraviolet wavelengths of interest and transmits the same to fiber optic bundle 22 which is part of fiber optic bundle 20 via output port 26 of source monochromator 14.

Figure 2:
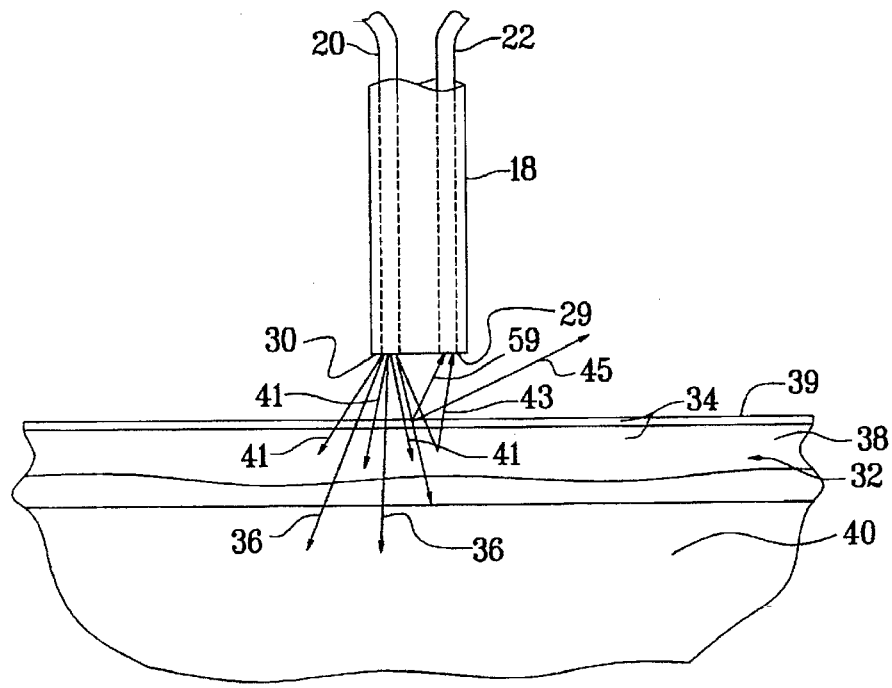
FIG. 2 is a front view of a singular fiber optic probe, and also showing returned light rays from the application of ultraviolet radiation to skin.

Referring to FIG. 2, the fiber optic probe 18 receives the ultraviolet radiation from source monochromator 12. The radiation is transmitted through fiber optic bundle 20. Naturally, different forms of probes will function with evaluator 10. Fiber optic bundle 20 transmits ultraviolet radiation to the skin 32 of the subjects during scans of both protected and unprotected skin 32. Fiber optic bundle 22 receives ultraviolet radiation that is reflected and diffused from skin 32 being used for the measurement. The intensity of the reflection depends upon the transmissivity of the skin, particularly its outer layers, and thus is a measure of the extent to which it passes harmful ultraviolet radiation.

The fiber optic probe 18 is shown most clearly in FIG. 2. This probe 18 is of the type wherein both the transmission or source portion coupled to bundle 20 and the detector portion coupled to bundle 22 are contained in the single housing of probe 18. As shown in FIG. 2, the fiber optic bundle 20 is the transmitting bundle and the fiber optic bundle 22 is the receiving bundle for returning diffused radiation to the detector monochromator for spectral evaluation. Light rays 33, emanating from the skin surface 39, are ultraviolet radiation which has been reflected directly off a layer of applied sunscreen 34, a portion 34a of which has penetrated into the epidermis 39. Some radiation 36 reaches the epidermis layer of skin 38 or the dermis layer 40 of the skin. With the sunscreen applied to the skin as shown in FIG. 2, certain rays 41 are absorbed by the sunscreen. With respect to rays 41, the sunscreen layer is effectively blocking the harmful ultraviolet rays.

In accordance with the invention it is recognized that because the susceptibility of the skin to sunburn is a function of the transmissivity of the skin in the dead epidermal layer which, especially when saturated and coated with sunscreen, blocks transmission of radiation to the living cells below, the effectiveness of a sunscreen can be measured by measuring the intensity of diffused light, such as rays 43, which are diffused upwardly through the sunscreen back toward probe 18. This is because these light rays 43 are subjected to the same attenuating physical effects that light rays 36 (which are diffused and reach the living cells) are subjected to. Thus the intensities of both rays 36 which damage the skin and rays 43 which are diffused toward probe 18 are both a function of the transmissivity of the sunscreen material. Thus, the measurement of the diffused light returned to probe 18 and bundle 22 will be useful to determine the effectiveness of the sunscreen. The measurement of a high intensity corresponds to low absorption by the sunscreen and thus a low SPF. Conversely, low intensities correspond to high SPF's.

Figure 3:
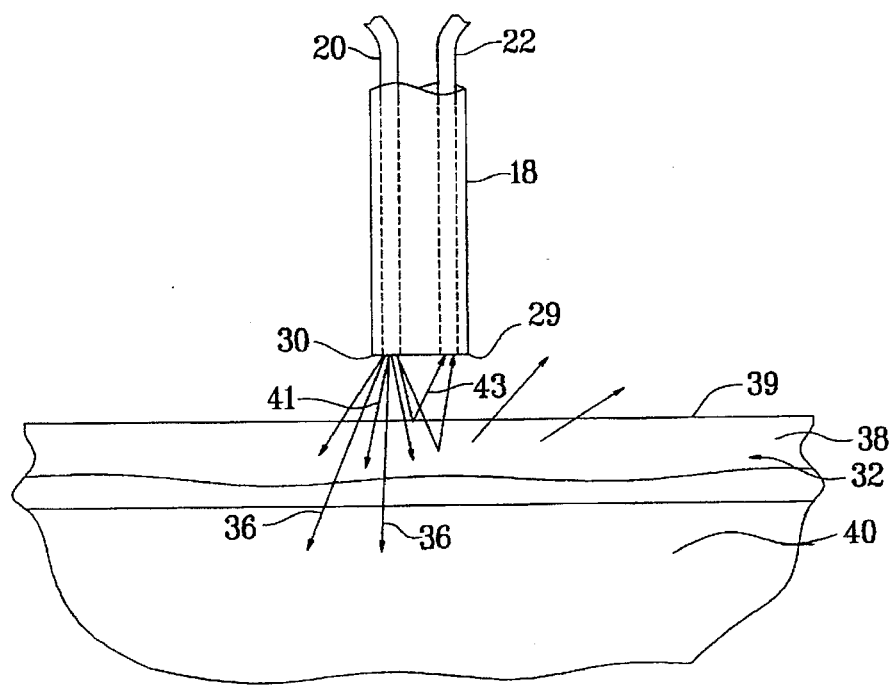
FIG. 3 is a view similar to the view of FIG. 2 of the evaluator, without sunscreen applied to the skin.

By way of contrast, FIG. 3 shows an epidermis layer of skin 38 and dermis layer 40, respectively, untreated with the sunscreen 34. As shown, the harmful ultraviolet rays 36 penetrate more deeply into the skin layers, thereby increasing the risk of sun damage. Likewise, more radiation 43 also exits the skin as strong unabsorbed rays and is collected by the probes 18.

From receiving fiber optic bundle 22, the diffused ultraviolet radiation is transmitted to detector monochromator 14. Fiber optic bundle 22 is connected to an input port 42 (FIG. 1) of the detector monochromator. The detector monochromator minimizes ambient noise processed by the system. In particular, monochromator 14 passes only light of the wavelength of light exiting from monochromator 12, thus substantially limiting the light output by monochromator 14 to detector photomultiplier tube 47. This results in detector 47 receiving substantially only light output by probe 18 and substantially not receiving light corresponding to ambient and other noise effects such as radiation reflected and diffused from the surface of the skin.

Figure 4:
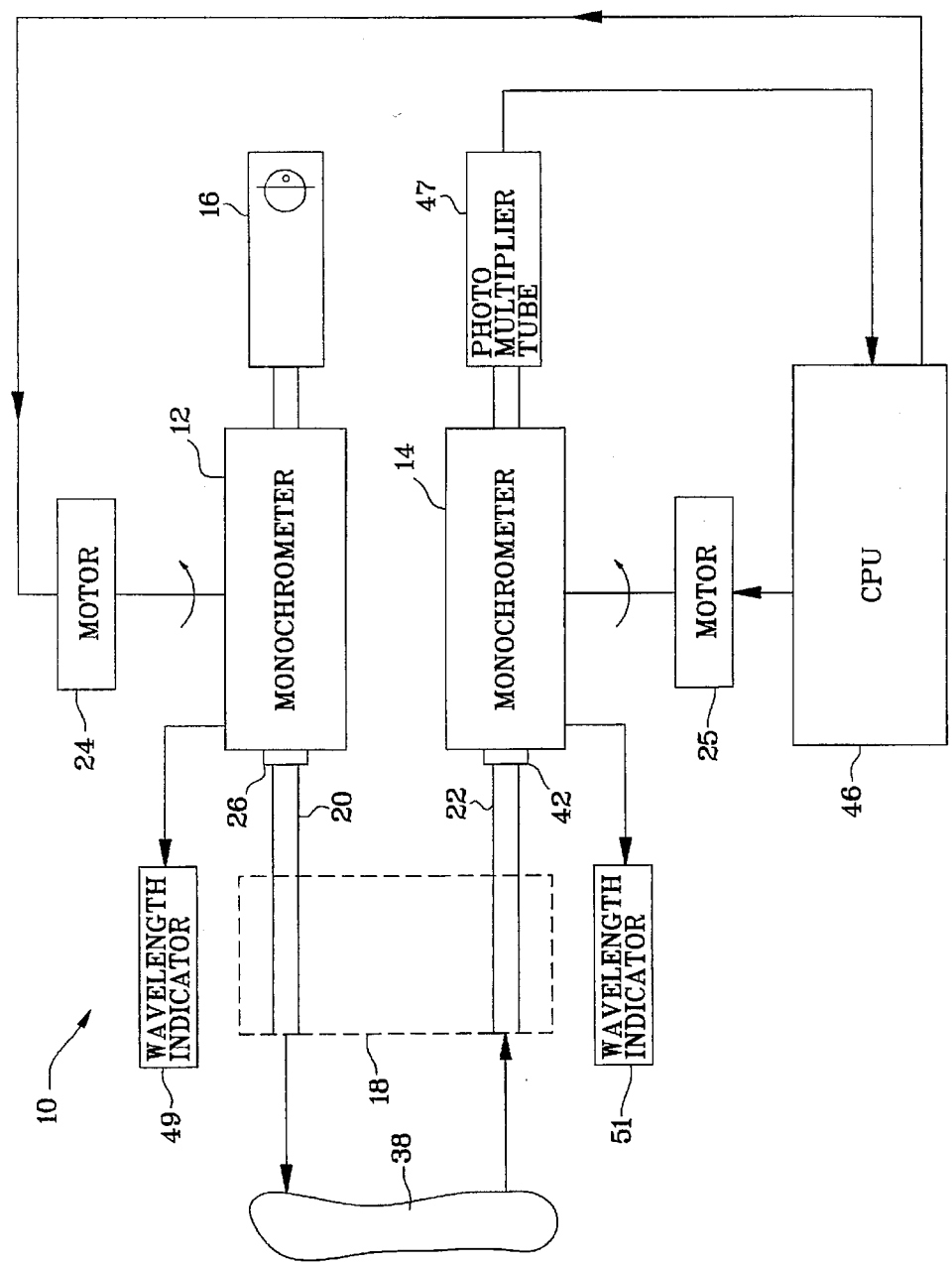
FIG. 4 is a schematic diagram of the ultraviolet radiation protection evaluation now showing its various components.

Referring to FIG. 4, the operation of this system may be understood. Light is provided by a lamp 16 which is optically coupled to source monochromator 12, which in turn sends light by way of bundle 20 to the skin 38 of the subject. Light is diffused and returned to bundle 22. Exiting bundle 22 is filtered by monochromator 14 which sends its output to photomultiplier tube 47. Computer 46 ensures that motors 24 and 25 adjust monochromators 12 and 14, respectively, to be at the same wavelength, thus ensuring a maximum signal to noise ratio at the input of photomultiplier tube 47 whose output is sent to computer 46. In accordance with the preferred embodiment of the invention, a scan with a light output from monochromator 12 and filtered by monochromator 14 is made through the UVA, the UVB or both ultraviolet bands, with computer 46 receiving the output of photomultiplier tube 47 during the wavelength scanning process. Computer 46 then computes the average sun protection factor for the desired range, whether it be the UVA, the UVB, or the combined entire ultraviolet range. Generally, such computation is based on accumulated physiological data which is gathered by scanning the skin of the subject in an area which has been treated with sunscreen and another area which has not been treated with sunscreen and then subjecting the skin of the subject to a conventional in vivo test of the type described above to determine what sun protection factors the readings produced by photomultiplier tube 47 correspond to. In principle, it may be said that such conventional testing methods are used to generate an interpretation of the data produced by photomultiplier tube 47, with a sufficiently large population being used to assure the reliability of the data. In any case, it is generally contemplated that the ratio of the average signal computed by computer 46 for untreated skin to the average value for treated skin will be a reliable indicator of sun protection factor or SPF.

Referring back to FIG. 1, some manual check in the operation of the system can be achieved by providing the monochromators with conventional wavelength indicators 49 and 51 which are mechanically coupled to their respective monochromators.

Figure 5:
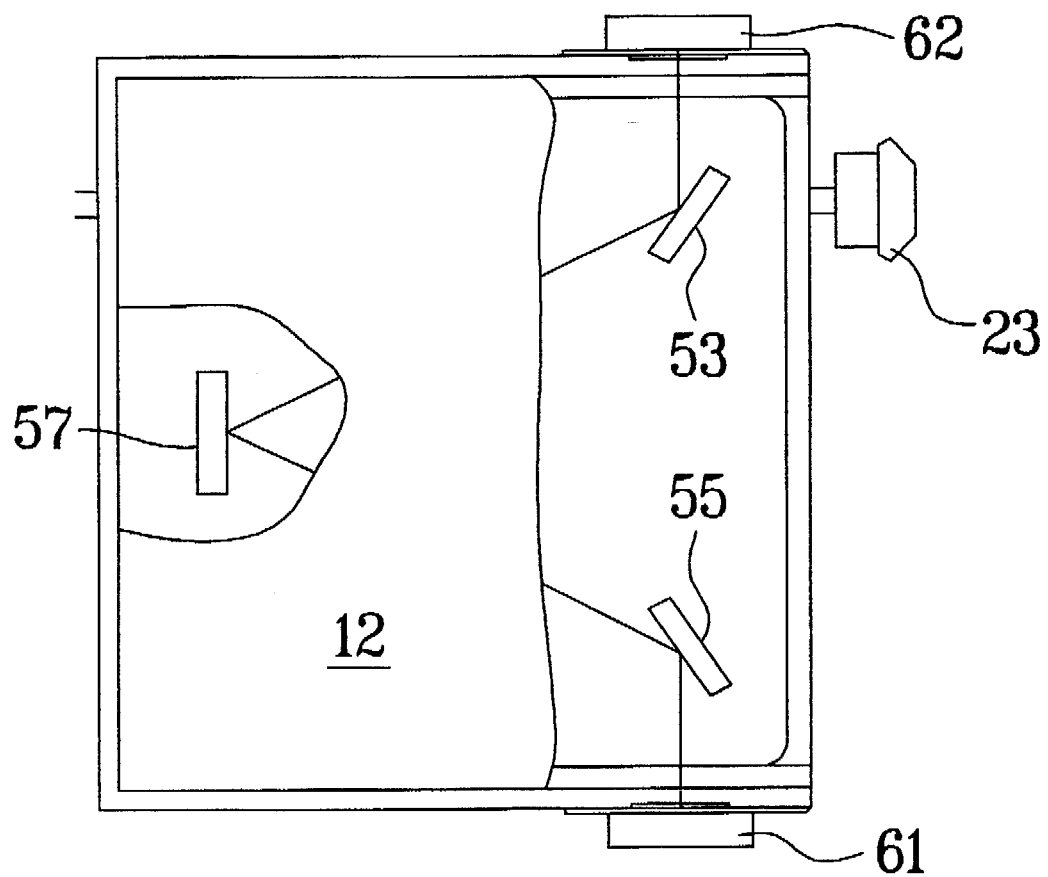
FIG. 5 is a front view of the monochromators used herein.

As alluded to above, the commercially available H-10 brand monochromator may be used for monochromator 12. Such a monochromator is illustrated in FIG. 5 and includes an input mirror 55, an output mirror 53 and a grating 57 with output coupling 61. Coupling 61 receives light input to the system from lamp 16 and coupling 62 mates with optical coupling 26.

As shown in FIG. 2, while doing a test with applied sunscreen, any ultraviolet radiation reflected from the surface is noise, as it corresponds to rays which do not reach the skin.

For example, as shown in FIG. 2 rays of light 59 reflecting from the sunscreen surface and constituting noise can enter the probe, thus forcing it to read it as light and radiation not blocked by the sunscreen, giving a falsely negative indication. Because of the vertical nature of the probe 18, it is possible that this noise will be read by the receiving fiber optic bundle and distort the reading of diffused reflection that is read by the detector monochromator 14. Rather, the probe should be protected from all but the deeper traveling, potentially more harmful ultraviolet rays 43. If greater accuracy is desired an inventive angled or bi-pole probe may be used. However, it is expected that even rigorous evaluation will show the noise usually associated with non contacting vertical probes will not greatly affect the results.

FIG. 5 shows a second embodiment, discussed below, which functions to alleviate this possibility of noise being directed to the detector monochromator.

Figure 6:
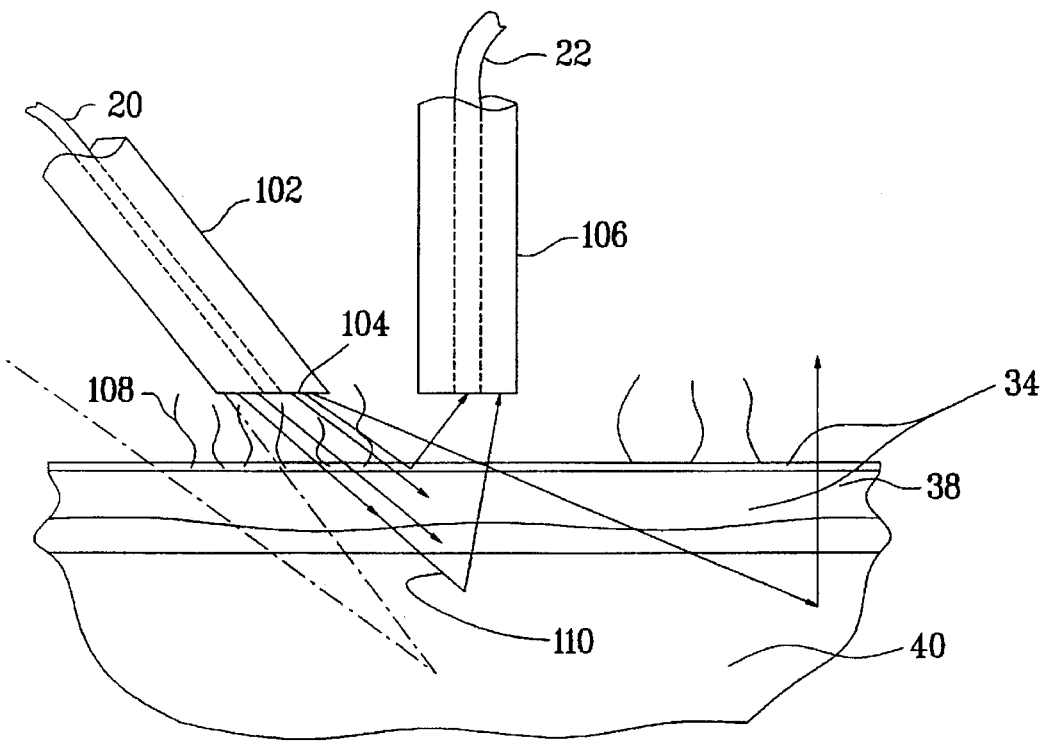
FIG. 6 is a front view of a second embodiment of a fiber optic probe having separate receiving and transmitting probes, wherein the receiving probe is angled.

The second embodiment, as shown in FIG. 6, incorporates the use of a bi-probe, which includes two separate probes, one for transmitting the ultraviolet radiation and a second probe for receiving the diffused and reflected ultraviolet radiation off the skin. As shown in FIG. 6, the source probe 102 has the transmission fiber optic bundle 20 therein and an angled leading edge 104 for directing the ultraviolet radiation at an angle to the epidermis skin layer 38. The second probe 106 is positioned substantially vertically, similar to the probe 18 in the first embodiment, but in this embodiment, having only the receiving fiber optic bundle 22 therein. Accordingly, the ultraviolet radiation is directed from the first probe 102 at an angle to the skin's surface 38.

As shown in FIG. 6, the ultraviolet radiation is reflected at an angle, unlike the vertical probe shown in FIG. 1, and the noise 108 is disbursed angularly and only in the area of the transmitting probe 102 so as substantially not to interfere with the receiving probe 106. The arrows 110 ending in the skin indicate ultraviolet radiation rays absorbed by the sunscreen and thus effective protection. The receiving probe 106 may be connected to the transmitting probe 102 so as to maintain an ideal distance between the probes. It is essential that the proper distance is determined for the testing specimen such that the dispersed and returned ultraviolet radiation can be received by the receiving probe 106.

Figure 7:
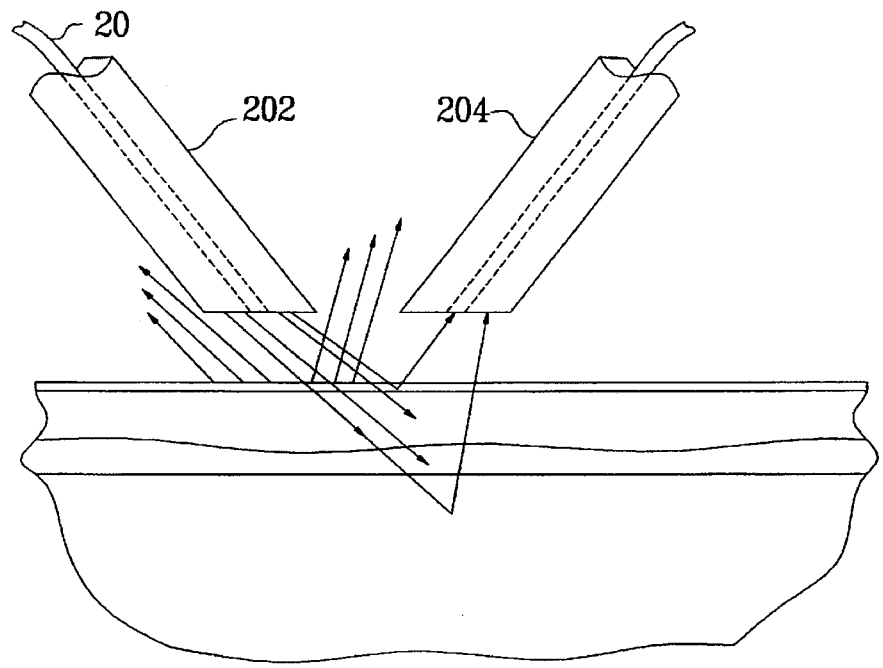
FIG. 7 is a front view of a third embodiment of a fiber optic probe wherein both the receiving and transmitting probes are angled.

A third embodiment is shown in FIG. 7, wherein two angled probes are used, one for receiving and one for transmitting. The first probe 202, is similar to the first probe 42 in the second embodiment wherein the ultraviolet radiation is transmitted from the fiber optic bundle. However, the second probe 204 is also angled so as to receive more of the diffused and the reflected ultraviolet radiation which tends to leave the skin at an angle. Therefore, the angular orientation of the probe 204 can be more efficient in gathering the reflected light and radiation. As with embodiment two, because of the angular nature of the first probe, misreadings based on noise from surface reflected light and radiation, are substantially avoided.

The evaluation machine 16 is used by first taking a spectral evaluation of the epidermis skin layer 38 prior to treatment with sunscreen 34. Accordingly, ultraviolet radiation is supplied from the light source to the source monochromator and probe 18 and finally to the unprotected epidermis skin layer 38 The reflected and diffused light and radiation is taken from the unprotected skin, passed through the fiber optic bundle 22 and to the detector monochromator 14 where a spectral evaluation of the light and radiation is performed. Such evaluation may be over a range of desired wavelengths or at a single wavelength for a reading of more limited value. At this point it is probable, that much of the analysis will indicate damaging ultraviolet radiation returned to the receiving portion of the probe into the detector monochromator 14, because it was not absorbed.

The epidermis skin layer 38 is then treated with a sunscreen 34 to be evaluated. Again, the ultraviolet radiation is supplied through the fiber optic probe 18 to the skin and received in the receiving portion of the probe and transmitted via bundle 22 to the detector monochromator. At this point, a spectral evaluation of the light and radiation reflected back to the detector monochromator is performed, and depending upon the rating of the sunscreen used, less harmful ultraviolet radiation is reflected and transmitted to the detector monochromator for spectral evaluation, because of increased absorption due to the sunscreen. This method of use is, of course, applicable to the angled probes of the embodiments of FIGS. 6 and 7, respectively.

The information obtained from the spectral evaluation by the detector monochromator is then transmitted to a computer 46 having software therein for the evaluation of the acquired readings. Accordingly, a ratio is calculated based upon the amount of ultraviolet radiation found in the spectrum for the skin without protection and for the skin with protection.

The sunscreen evaluating apparatus 10 be calibrated by finding an initial value for sun protection which is indicative of the body's natural capacity to protect itself from sun damage. As alluded above, this can be determined by first taking readings using apparatus 10 for both the untreated and treated skin and then performing conventional in vivo testing, wherein the same live human subject is subjected to ultraviolet radiation until a burn is achieved, to determine the precise quantitative interpretation of those readings. The spectral analysis associated with such testing can be used as a base for determining the ratings of the various sunscreens. Accordingly, the sunscreens are rated by a numeral as a multiple of the number of times the sunscreen is effective against ultraviolet radiation in comparison to the body's natural ability for protection.

Figure 8:
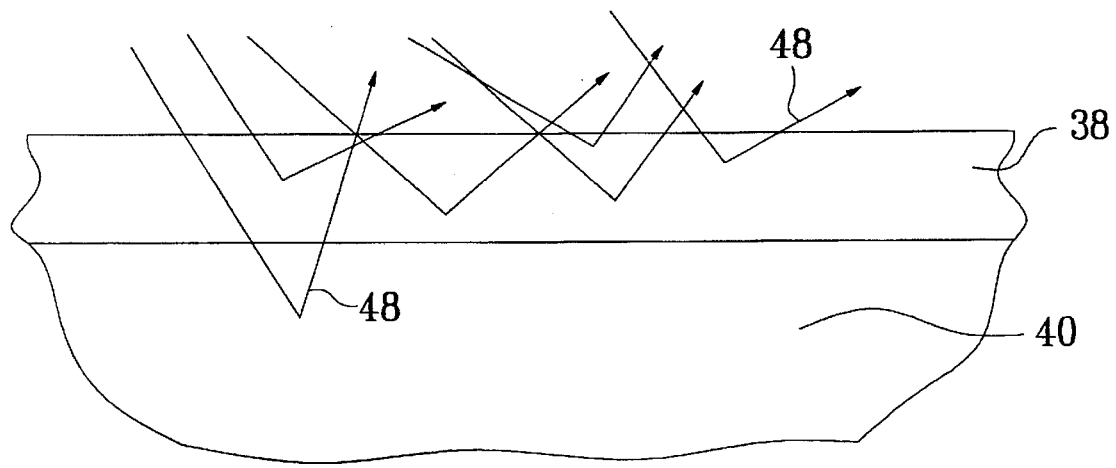
FIG. 8 illustrates ultraviolet radiation incident to skin having no sunscreen thereon.
Figure 9:
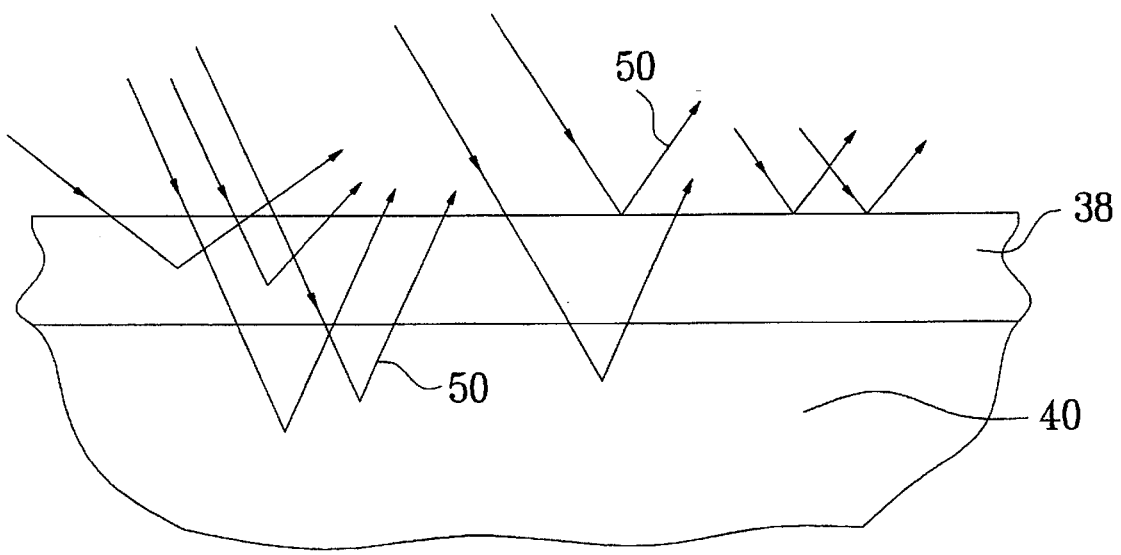
FIG. 9 illustrates ultraviolet radiation incident to skin having no sunscreen thereon and less natural protection than the skin shown in FIG. 6.

Because humans differ as to their skin's ability to benefit from sunscreen as well as its natural ability to protect against damage from the sun, as discussed below in connection with in FIGS. 8 and 9, based on size, weight, sex and age, the apparatus 10 can be used to create new standards for specified types of people or for determining in what manner current sunscreens react with people who are overweight, older, male or female, dark skinned or fair skinned. FIG. 8 shows, for example, a skin type wherein the natural ultraviolet protection, at a known intensity, allows minimal penetration of harmful rays to the living skin, indicated by the medium depth to which the rays 48 extend into the epidermis skin layer 38 and dermis layer 40. Referring to FIG. 9, and assuming the same sun intensity, the harmful rays are shown to travel deeper into the skin, causing more damage as indicated by the rays 50 extending deeper into the epidermis skin layer 38 and dermis layer 40 as compared to FIG. 8. As such, the current standards can be used as a starting point and additional factors discovered through testing can be used along with this technology for groups of individuals to determine their actual needed sun protection. The apparatus may have different calibration algorithm stored in computer 46 for various sexes, skin colorings, and so forth, with the algorithm determined by statistical testing in the relevant population.

Figure 10:
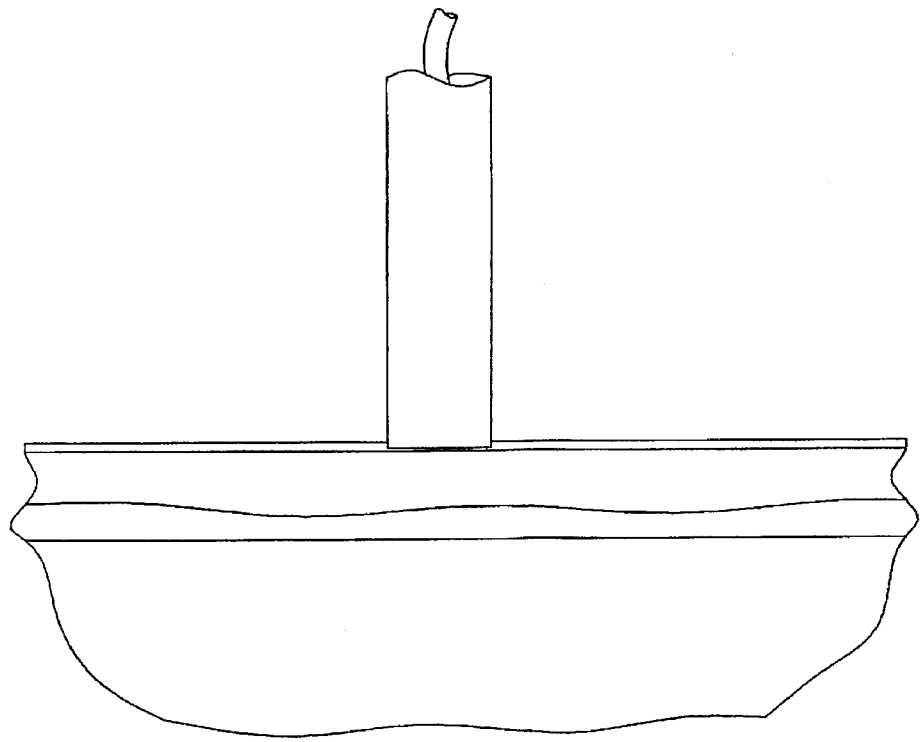
FIG. 10 is a front view of a fiber optic probe similar to that shown in FIG. 1, showing the probe contacting the skin.
Figure 11:
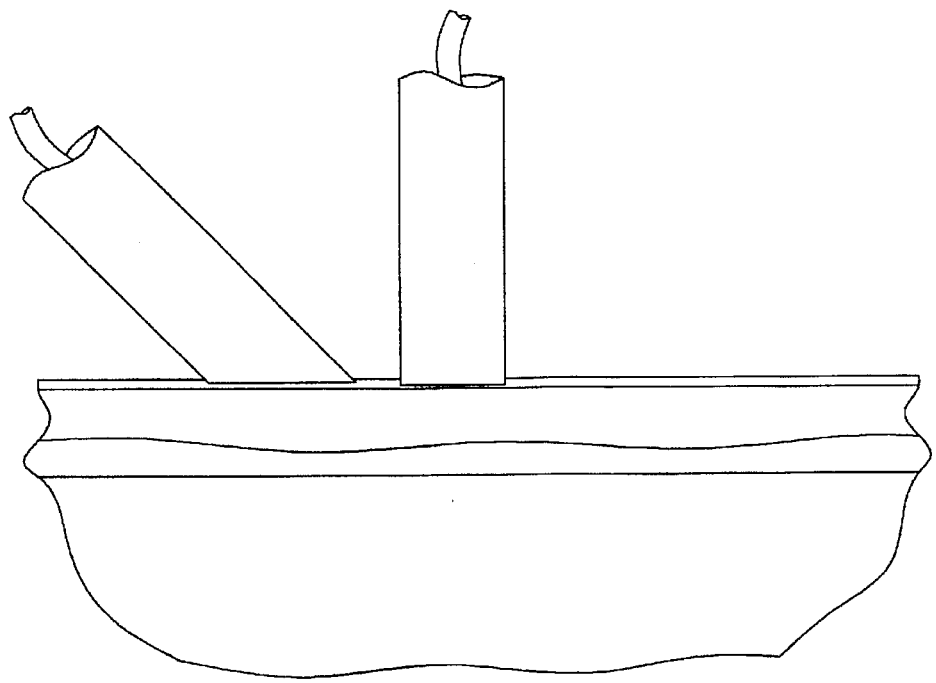
FIG. 11 is a front view of the fiber optic probe in similar to that shown in FIG. 5, showing the probes contacting the skin.

In principle, the noise caused by direct reflection can be minimized by putting the probe in contact with the skin of the subject. To the extent that the sunblocking capacity of any oily film resting above the skin is minimal, such an approach has the effect of substantially eliminating signal distortion caused by direct reflection of light. This approach may be applied to both vertical type probes as illustrated in FIG. 10 and oblique probes as illustrated in FIG. 11.

While an illustrative embodiment of the ultraviolet radiation protection evaluator has been described above, it is, of course, understood that various modifications will be apparent to those of ordinary skill in the art. Such modifications are within the spirit and scope of the invention, which is limited and defined only by the appended claims.

We claim:

1. An ultraviolet radiation protection evaluator for nondestructive evaluation of sun protection factor (spf) for sun screen or tanning preparations which are used to treat skin against sunburn, comprising:
    (a) an ultraviolet light source for applying multiple applications of ultraviolet light to treated and untreated skin of a subject;
    (b) an ultraviolet light detector for detecting ultraviolet light returned by said treated and untreated skin; and
    (c) a spectral analyzer connected to and in optical communication with said detector, said spectral analyzer for receiving said returned ultraviolet light from applications of light to treated and untreated skin and conducting a spectral analysis of the treated and untreated skin, for determining the amount of ultraviolet light filtered out by said treated skin and generating an output of a measure of the sun protection factor.

2. An ultraviolet radiation protection evaluator as in claim 1, further comprising a computer for receiving the output of said spectral analyzer, and for categorizing and evaluating said spectral analysis in terms of the amount of ultraviolet light filtered out by said skin to determine the amount of ultraviolet light absorbed by said skin.

3. The ultraviolet radiation protection evaluator as in claim 2, wherein said source and detector is comprised of a fiber optic probe which receives and transmits ultraviolet light.

4. An ultraviolet radiation protection evaluator as in claim 2, wherein said ultraviolet light source includes a fiber optic probe having an angled application head and said detector includes a second fiber optic probe having an angled receiving head.

5. An ultraviolet radiation protection evaluator as in claim 4, wherein said spectral analyzer includes a monochromator adapted to receive said filtered ultraviolet light and perform a spectral analysis on said filtered ultraviolet light.

6. An ultraviolet radiation protection evaluator as in claim 5, wherein said source receives said ultraviolet light from a monochromator adapted to separate said ultraviolet light from a radiation source and transmit said ultraviolet light to said fiber optic probe of said ultraviolet light source.

7. An ultraviolet radiation protection evaluator as in claim 1, wherein said ultraviolet light source includes a fiber optic probe having an angled application head, and said detector includes a second fiber optic probe.

8. An ultraviolet radiation protection evaluator as in claim 1, wherein said spectral analyzer includes a monochromator for separating ultraviolet light from a light mixture received by a receiving probe providing light to said spectral analyzer.

9. An ultraviolet radiation protection evaluator as in claim 1 wherein at least one of said ultraviolet light source and said ultraviolet light detector includes a fiber optic probe.

10. A method for evaluating the level of protection against ultraviolet damage of a sunscreen preparation for skin by comparing optical properties of skin with and without said sunscreen applied thereto, comprising the steps of:
    (a) applying light to unprotected skin from a source and receiving returned light from said skin using a light detector;
    (b) transmitting said returned light from said light detector to a spectral analyzer,
    (c) treating the skin by applying sunscreen to the skin;
    (d) applying light from said source to said skin treated with said sunscreen applied thereon and receiving returned light from the skin with said sunscreen applied thereon using said light detector;
    (e) transmitting said light returned in response to said application of light to said treated skin from said detector to a spectral analyzer for determining an amount of light filtered by said skin having the sunscreen thereon in comparison to an amount of light filtered by skin not having said sunscreen; and
    (f) transmitting the results from said spectral analysis to a computer for determining a level of protection given by said sunscreen.

11. A method as in claim 10, wherein the light being applied is ultraviolet light.

12. A method as in claim 10, wherein said spectral analysis is performed on the ultraviolet components of said returned light.

13. An ultraviolet radiation protection evaluator for evaluating a protection value of an ultraviolet radiation protector applied to skin, comprising;
    an ultraviolet light projector including an ultraviolet light source for generating an ultraviolet light, a source probe for directing the ultraviolet light to skin having an ultraviolet radiation protector applied thereto and a transmission fiber optic bundle for transmitting the ultraviolet light from the ultraviolet light source to the source probe; an ultraviolet light detector including a receiving probe for receiving filtered ultraviolet light from the skin having the ultraviolet radiation protector applied thereto, a spectral analyzer receptive of the filtered ultraviolet light for conducting a spectral analysis of the same so as to determine an amount of the filtered ultraviolet light received from the skin to evaluate a protection value of the ultraviolet radiation protector and a receiving fiber optic bundle for transmitting the received filtered ultraviolet light from the receiving probe to the spectral analyzer.

14. An ultraviolet radiation protection evaluator according to claim 13; wherein the source probe has an oblique angled leading edge for directing the ultraviolet light at an oblique angle relative to the skin to reduce noise light received along with the filtered ultraviolet light.

15. An ultraviolet radiation protection evaluator according to claim 13; wherein the source probe and the receiving probe are joined so that a proper distance is maintained between the skin and the source probe and the receiving probe to reduce a noise light received along with filtered ultraviolet light.

16. An ultraviolet radiation protection evaluator according to claim 13; wherein the receiving probe has an oblique angled leading edge for receiving the filtered ultraviolet light at an oblique angle relative to the skin to reduce a noise light received along with filtered ultraviolet light.

17. An ultraviolet radiation protection evaluator according to claim 13; wherein the directing light probe has an oblique angled leading edge for directing the ultraviolet light at an oblique angle relative to the skin; and the receiving light probe has an oblique angled leading edge for receiving the filtered ultraviolet light at an oblique angle relative to the skin so as to reduce a noise light received along with the filtered ultraviolet light.

18. An ultraviolet radiation protection evaluator according to claim 13; wherein the spectral analyzer includes a monochromator for separator ultraviolet light from a light mixture received by the receiving probe.

19. An ultraviolet radiation protection evaluator according to claim 13; wherein the ultraviolet light source includes a monochromator for separator ultraviolet light from a light mixture generated by the ultraviolet light source.

20. A method of evaluating the skin protection characteristic of a sunscreen comprising the steps of:

(a) applying and detecting light having a wavelength against which protection is desired to the skin of a subject in a particular area of the skin;

(b) applying the sunscreen to be tested to said particular area;

(c) repeating the application and detection of light having said wavelength to said particular area with sunscreen applied to it; and (d) comparing the detected amount of light returned by the skin before and after application of said sunscreen and determining the extent to which said light of said wavelength has been absorbed to create a measurement of said skin protection characteristics.

21. A method as in claim 20, wherein the sunscreen is applied to said untreated skin and the application of light to treated skin is made to the same portion of the skin to which said light is applied when said light is applied to untreated skin.

* * * * *